(12) United States Patent
Huse et al.

(10) Patent No.: US 6,348,194 B1
(45) Date of Patent: Feb. 19, 2002

(54) TUMOR SPECIFIC INTERNALIZING ANTIGENS AND METHODS FOR TARGETING THERAPEUTIC AGENTS

(75) Inventors: William D. Huse, Del Mar; Jeffry D. Watkins, Encinitas, both of CA (US)

(73) Assignee: Ixsys Incorporated, San Diego, CA (US)

( * ) Notice: Subject to any disclaimer, the term of this patent is extended or adjusted under 35 U.S.C. 154(b) by 0 days.

(21) Appl. No.: 08/555,684

(22) Filed: Nov. 13, 1995

(51) Int. Cl.$^7$ .................. A61K 39/395; A61K 39/00; C07K 16/28; A01N 43/04

(52) U.S. Cl. .................. 424/143.1; 424/277.1; 424/155.1; 424/179.1; 424/183.1; 424/1; 424/138.1; 530/388.8; 530/389.7; 530/391.7; 514/25

(58) Field of Search .................. 424/143.1, 179.1, 424/183.1, 277.1, 181.1, 155.1, 138.1; 514/25; 530/391.7, 388.8, 389.7

(56) References Cited

PUBLICATIONS

"Keystone Symposium on Complex Carbohydrates in Biology and Medicine: Cancer," *Cancer Research* 55:450–453 (1995).

Calvo, Dominica and Vega, Miguel A., "Identification, Primary Structure, and Distribution of CLA–1, a Novel Member of the CD36/LIMPII Gene Family," *J. Biol. Chem.* 268(25) :18929–18935 (1993).

Chauhan et al., "Expression of Cathepsin L in Human Tumors," *Cancer Res.* 51 : 1478–1481 (1991).

Dubois et al., "Estrogen and Insulin Modulation of Intracellular Insulin–like Growth Factor Binding Proteins in Human Breast Cancer Cells: Possible Involvement in Lysosomal Hydrolases Oversecretion," *Biochemical and Biophysical Research Comm.* 192(1) :295–301 (1993).

Fukuda, Minoru, "Lysosomal Membrane Glycoproteins," *J. Biol. Chem.* 266(32) :21327–21330 (1991).

Garrigues et al., "Anti–Tumor Antibody BR96 Blocks Cell Migration and Binds to a Lysosomal Membrane Glycoprotein on Cell Surface Microspikes and Ruffled Membranes," *J. Cell Biol.* 125(1) :129–142 (1994).

Harter, Cordula and Mellman, Ira, "Transport of the Lysosomal Membrane Glycoprotein lgp120 (lgp–A) to Lysosomes Does Not Require Appearance on the Plasma Membrane," *J. Cell Biol.* 117(2) :311–325 (1992).

Hellström et al., "Highly Tumor–reactive, Internalizing, Mouse Monoclonal Antibodies to Le$^y$–related Cell Surface Antigens," *Cancer Research* 50:2183–2190 (1990).

Hotta et al., "Molecular Cloning and Characterization of an Antigen Associated with Early Stages of Melanoma Tumor Progression," *Cancer Research* 48:2955–2962 (1988).

Jirtle et al., "Increased Mannose 6–Phosphate/Insulin–like Growth Factor II Receptor and Transforming Growth Factor β1 Levels during Monoterpene–induced Regression of Mammary Tumors," *Cancer Research* 53:3849–3852 (1993).

Johnson et al., "The Role of Cathepsin D in the Invasiveness of Human Breast Cancer Cells," *Cancer Research* 53:873–877 (1993).

Marken et al., "Cloning and expression of the tumor–associated antigen L6," *Proc. Natl. Acad. Sci. USA* 89:3503–3507 (1992).

Mathieu et al., "Estradiol Down–Regulates the Mannose–6–Phosphate/Insulin–Like Growth Factor–II Receptor Gene and Induces Cathepsin–D in Breast Cancer Cells: A Receptor Saturation Mechanism to Increase the Secretion of Lysosomal Proenzymes," *Molecular Endocrinology* 5(6) :815–822 (1991).

Metzelaar et al, "CD63 Antigen," *J. Biol. Chem.* 266(5) :3239–3245 (1991).

Parton et al., "Regulated Internalization of Caveolae," *J. Cell Biol.* 127(5) :1199–1215 (1994).

Redhead, "A ubiquitous 64–kDa protein is a component of a chloride channel of plasma and intracellular membranes," *Proc. Natl. Acad. Sci. USA* 89:3716–3720 (1992).

Rijnboutt et al., "Mannose 6–Phosphate–independent Membrane Association of Cathepsin D, Glucocerebrosidase, and Sphingolipid–Activating Protein in HepG2 Cells," *J. Biol. Chem.* 266(8) :4862–4868 (1991).

Rozhin et al., "Pericellular pH Affects Distribution and Secretion of Cathepsin B in Malignant Cells," *Cancer Research* 54:6517–6525 (1994).

(List continued on next page.)

*Primary Examiner*—Paula K. Hutzell
*Assistant Examiner*—Geetha P. Bansal
(74) *Attorney, Agent, or Firm*—Campbell & Flores LLP

(57) ABSTRACT

The invention provides a method of reducing the proliferation of a neoplastic cell. The method consists of contacting the neoplastic cell with a cytotoxic or cytostatic binding agent specifically reactive with an aberrantly expressed vesicular membrane associated neoplastic cell specific internalizing antigen. The neoplastic cell specific internalizing anitgen can be selected from the group consisting of lamp-2 and limp II families of lysosomal integral membrane proteins. Also provided is a method of intracellular targeting of a cytotoxic or cytostatic agent to a neoplastic cell population. The method consists of administering to an individual containing a neoplastic cell population a cytotoxic or cytostatic binding agent specifically reactive with an aberrantly expressed vesicular membrane associated neoplastic cell specific internalizing antigen that is expressed by the neoplastic cell population, wherein the cytotoxic or cytostatic binding agent is bound by the neoplastic cell specific internalizing antigen and is internalized into the intracellular compartment. A method of reducing tumor growth through the intracellular targeting of a cytotoxic agent is also provided.

13 Claims, No Drawings

OTHER PUBLICATIONS

Scheper et al., "Overexpression of a $M_r$ 110,000 Vesicular Protein in Non–P–Glycoprotein–mediated Multidrug Resistance," *Cancer Research* 53:1475–1479 (1993).

Sleat et al., "Increased Levels of Glycoproteins Containing Mannose 6–Phosphate in Human Breast Carcinomas," *Cancer Research* 55:3424–3430 (1995).

Szala et al., "Molecular cloning of cDNA for the human tumor–associated antigen CO–029 and identification of related transmembrane antigens," *Proc. Natl. Acad. Sci. USA* 87:6833–6837 (1990).

Trail et al., "Cure of Xenografted Human Carcinomas by BR96–Doxorubicin Immunoconjugates," *Science* 261:212–215 (1993).

Vega et al., "Cloning, Sequencing, and Expression of a cDNA Encoding Rat LIMP II, a Novel 74–kDa Lysosomal Membrane Protein Related to the Surface Adhesion Protein CD36," *J. Biol. Chem.* 266(25):16818–16824 (1991).

Zhao et al., "Correlation between Mannose–6–phosphate/IGFII Receptor and Cathepsin D RNA Levels by in Situ Hybridization in Benign and Malignant Mammary Tumors," *Cancer Research* 53:2901–2905 (1993).

Rosenblum et al 1992 Mol. Biother. 4:122–129.*

Geissler et al 1992 Cancer Res. 52:2907–2915.*

Wu 1997 Br. J. Cancer 75(9):1347–1355.*

Garrigues et al 1994 J. Cell Biol. 125(1):129–142.*

* cited by examiner

TUMOR SPECIFIC INTERNALIZING ANTIGENS AND METHODS FOR TARGETING THERAPEUTIC AGENTS

Throughout this application various publications are referenced within parentheses. The disclosures of these publications in their entireties are hereby incorporated by reference in this application in order to more fully describe the state of the art to which this invention pertains.

BACKGROUND OF THE INVENTION

The present invention relates generally to lysosomal and vesicular secretory pathways and, more particularly, to tumor antigen discovery and to methods of intracellularly targeting therapeutic agents.

Neoplastic cell transformations, or cancer, is a disease which results in more than 2.3 million deaths annually, or greater than 20% of all deaths reported to the World Health Organization in the industrialized countries. Neoplastic cell transformations manifests as a group of cells that proliferate outside the normal growth control mechanisms and can be considered a collection of many different diseases which differ in their genetic basis, progression and clinical outcome.

The standard methods of treatment for cancer currently include surgery, radiation therapy, and chemotherapy using cytotoxic drugs. Such methods can be effective if treatment is initiated early enough. However, each therapeutic approach comes with inherent problems. Perhaps the most significant of these problems include unacceptable toxic side effects and the lack of complete surgical removal of the entire neoplastic growth. An additional problem in treating cancer results from metastasis of the primary tumor to secondary sites if treatment is not complete or initiated early before substantial progression of the disease.

Immunotherapy is one approach to overcome the lack of specificity inherent in today's current treatments. In general, immunotherapy offers several advantages which include not only the ability to generate antibodies to essentially any desired antigen but also the ability to produce antibodies that exhibit high specificity and binding affinity to the particular antigen of interest. This high specificity and binding affinity allows specific targeting of therapeutic agents to essentially all diseased cells in which there is an identified and specific antigen marker. However, any cross reactivity of the antibody to other antigens or the presence of significant quantities of the marker antigen on the surface of non-diseased cells will lead to binding and the unfortunate targeting of toxic agents to normal cell types. Thus, the specificity and efficiency of targeting is the combined function of both the specificity of the antibody and the reliability of the antigen marker.

The discovery of such putative antigen markers generally occurs through a fortuitous observation, or can result from a labor intensive effort to specifically screen and identify putative tumor specific antigens. The latter of such efforts generally involves either the generation of a panel of antibodies against tumor cell surface antigens and then screening of the panel against tumor and control cells to determine which antibodies may be significantly reactive and specific for a particular tumor cell type. The percentage of those antibodies screened that are ultimately identified as being reactive with tumor cell specific markers is usually a very low percentage.

There are now a number of antibodies which recognize cell surface antigens reported to be preferentially expressed on neoplastic cells. These antibodies are increasingly being applied in the clinic as diagnostic tools and as potential therapeutic treatments. However, even with highly specific antibodies or antigen markers there still remains at least one major problem which leads to several side effects and a lower quality of life. This problem results from the toxicity of the therapeutic agents that are conjugated to the tumor specific antibodies. Such agents generally include radioisotopes which are highly toxic to all cells which come in contact with the antibody conjugate and especially to the neighboring cells around the targeted tumor cell mass. One possibility to overcome such side effects would be to selectively introduce the toxic agent intracellularly. Such an intracellular targeting scheme would require not only the identification of a tumor cell specific marker and generation of a highly specific antibody, but also that the marker antigen undergo internalization to avoid toxic side effects to surrounding normal cells.

Lymphocyte marker antigens have been identified which undergo internalization from the cell surface. Many of these lymphocyte antigens, if not all of them, are cell surface proteins which include cytokine receptors, T cell receptors, major histocompatibility and the like. In regard to cells outside of the lymphocyte lineage, there are relatively very few internalizing antigens that are known to exist for solid tumors. One example is the transferrin receptor which naturally functions as a carrier of iron between the extracellular and intracellular environment. Another example is the mannose-6-phosphate receptor which directs soluble lysosomal enzymes to prelysosomal compartments. Antigens of this category which are known to normally cyclize between different cellular locations also generally exhibit poor tumor cell specificity.

Of those few antigens that are currently being evaluated as internalizing antigens for solid tumors, most if not all were unfortunately discovered by serendipity. For example, the Le$^y$ antigen was initially characterized as being an altered glycosylation product found on the cell surface of tumorigenic cells. Other antigens include lysosomal membrane proteins such as those belonging to the lamp-1 or lamp-3 families. The Le$^y$ antigen is now thought to be an altered glycosylation product which is primarily associated with lamp-1. However, because these antigens were discovered independently of one another and their full potential could not be appreciated for the therapeutic benefit of essentially many different types of cancers.

Thus, there exists a need for the therapeutic treatment of tumors to enable the consistent and efficient identification of novel internalizing antigen markers. Such novel internalizing antigens can be used to enhance the specificity of immunotherapeutic approaches. The present invention satisfies this need and provides related advantages as well.

SUMMARY OF THE INVENTION

The invention provides a method of reducing the proliferation of a neoplastic cell. The method consists of contacting the neoplastic cell with a cytotoxic or cytostatic binding agent specifically reactive with an aberrantly expressed vesicular membrane associated neoplastic cell specific internalizing antigen. The neoplastic cell specific internalizing anitgen can be selected from the group consisting of lamp-2 and limp II families of lysosomal integral membrane proteins. Also provided is a method of intracellular targeting of a cytotoxic or cytostatic agent to a neoplastic cell population. The method consists of administering to an individual containing a neoplastic cell population a cytotoxic or cytostatic binding agent specifically reactive with an aberrantly expressed vesicular membrane associated neoplastic cell specific internalizing antigen that is expressed by the neoplastic cell population, wherein the cytotoxic or cytostatic binding agent is bound by the neoplastic cell specific internalizing antigen and is internalized into the intracellular compartment. A method of reducing tumor growth through the intracellular targeting of a cytotoxic agent is also provided.

DETAILED DESCRIPTION OF THE INVENTION

This invention is directed to novel methods for targeting immunoconjugates to neoplastic cell populations. The methods rely on the identification and utilization of neoplastic cell specific internalizing antigens to achieve high specificity for the target cell population. One advantage of the methods is that they employ cell surface antigens which undergo internalization of the bound immunoconjugate into the cytoplasm. This internalization provides greater specificity and therapeutic efficacy since toxic side effects to neighboring cells is significantly reduced.

In one embodiment, lysosomal membrane proteins are used to specifically target toxic antibody conjugates to neoplastic cell populations. The lysosomal membrane proteins can be found expressed on the plasma membrane at very low levels in normal cell populations but become significantly elevated on the cell surface in neoplastic cells of the same lineage. Although surface expression of these lysosomal membrane proteins is elevated in the neoplastic phenotype, these proteins are still internalized and recycled as observed in normal cells for the endocytic pathway. These two characteristics not only confer high specificity to the therapeutic approach but also result in greater efficacy since toxic agents can be employed which have a direct and specific effect on cell viability.

As used herein, the term "neoplastic cell" is intended to mean a cell that exhibits an abnormal morphological or proliferative phenotype. In vitro such cells are characterized by anchorage independent cell growth and loss of contact inhibition whereas in vivo such cells can be characterized by, for example, an abnormal new growth of tissue, the cells of which can tend to invade surrounding tissue and metastasize to other body sites.

As used herein, the term "neoplastic cell specific internalizing antigen" is intended to mean a class of proteins which are membrane associated and preferentially localized in non-neoplastic cells to the lysosomal or other intracellular vesicular compartments. However, in neoplastic cells, such internalizing antigens are expressed at elevated levels on the plasma membrane compared to non-neoplastic cells and as such are neoplastic cell specific antigens. Thus, such antigens can also be described as aberrantly expressed membrane associated vesicular antigens. These antigens are aberrantly expressed on the plasma membrane of neoplastic cells and are capable of undergoing internalization. Vesicular compartments can include, for example, membranous subcellular organelles and structures such as the endoplasmic reticulum, the golgi apparatus, lysosomes, endosomes, coated pits and caveolae. Membrane association includes, for example, integral membrane proteins as well as peripheral membrane associated proteins. Proteins which are anchored to the membrane through glycolipid modification and the like are also included within the definition of lysosomal membrane associated proteins.

The definition of neoplastic cell specific internalizing antigen is intended to include those known lysosomal membrane glycoproteins which can be classified into the general categories known by those skilled in the art as lamp-2 and limp II. Cla-1 is a specific example of a limp II family member. The initial classification of these molecules has been described in Fukuda, M. *J. Biol. Chem.* 266:21327–21330, (1991). Lysosomal membrane associated proteins which are not yet, or have not been categorized into these classifications are also intended to be included within the definition of a neoplastic cell specific internalization antigen. Such molecules include, for example, p110, vacuolar-$H^+$-ATPase, acetyl CoA:α-glucosaminide N-acetyltransferase, prosaposin, procathepsin L receptor and lysosomal acid phosphatase. Further, lysosomal proteins which are subsequently identified to be in these lysosomal protein families as well as other lysosomal or vesicular families, including for example, the lamp-1 and lamp-3 families of lysosomal membrane glycoproteins are also intended to be included within the definition of the term so long as the molecule exhibits the characteristics of being a membrane associated protein expressed at elevated levels on the plasma membrane in neoplastic cells and can be internalized.

Thus, the specific tumor associated antigens known as lamp-1, CD63 (ME491), CO-029, and L6 are excluded from neoplastic cell specific internalizing antigen as defined above. Similarly, known soluble lysosomal enzymes are also excluded from the definition.

As used herein, the term "binding agent" refers to a molecule which exhibits specific binding activity toward a neoplastic cell specific internalizing antigen. Such a binding molecule can include a variety of different types of molecules including, for example, macromolecules and small organic molecules. The type of binding agent selected will depend on the need. Small molecule binding agents can include, for example, receptor ligands, antagonists and agonists. Macromolecules can include, for example, peptide, polypeptide and protein, nucleic acids encoding polypeptide binding agents, lectins, carbohydrate and lipids. It is understood that the term includes fragments and domains of the agent so long as binding function is retained. Similarly, the boundaries of the domains are not critical so long as binding activity is maintained. In the specific example where the binding agent is a peptide, polypeptide or protein, such binding proteins can include monomeric or multimeric species. Heteromeric binding proteins are a specific example of multimeric binding proteins. It is understood that when referring to multimeric binding proteins that the term includes fragments of the subunits so long as assembly of the polypeptides and binding function of the assembled complex is retained. Heteromeric binding proteins include, for example, antibodies and fragments thereof such as Fab and $F(ab')_2$ portions, T cell receptors, integrins, hormone receptors and transmitter receptors.

The terms "cytotoxic" and "cytostatic" when used to characterize a binding agent is intended to mean that the binding agent exhibits or has been modified to exhibit cytotoxic or cytostatic properties. For example, there are many known toxins or drugs which are known by those skilled in the art to exhibit these properties. Specific examples of cytotoxic and cytostatic agents include, for example, pokeweed antiviral protein, abrin, ricin and each of their A chains, doxorubicin, cisplastin, Iodine-131, Yttrium-90, Rhenium-188, Bismuth-212, Taxol, 5-Fluorouracil VP-16, Bleomycin, methotrexate, vindesine, adriamycin, vincristine, vinblastine, BCNU, mitomycin and cyclophosphamide and certain cytokines such as TNF-α and TNF-β. Thus, cytotoxic or cytostatic agents can include, for example, radionuclides, chemotherapeutic drugs, proteins and lectins. Any of these agents can be attached to a binding agent for the cytoplasmic targeting of therapeutic agents to neoplastic cells.

As used herein, the term "specifically reactive" when used in reference to a binding agent refers to the discriminatory binding of the binding agent to an aberrantly expressed vesicular membrane associated neoplastic cell specific internalizing antigen. For such binding to be discriminating, the binding agent will not substantially cross react, or can be made not to substantially cross react with other surface markers which are not the particular neoplastic cell specific internalization antigen. Specific reactivity can include binding properties such as binding specificity, binding affinity and binding avidity.

The invention provides a method of reducing the proliferation of a neoplastic cell. The method consists of contacting the neoplastic cell with a cytotoxic or cytostatic binding agent which is specifically reactive with a neoplastic cell specific internalizing antigen.

Among the many phenotypes associated with neoplasia, a large percentage result from the deregulation of the cell cycle which leads to enhanced proliferative phenotype. Apart from the altered expression or activity of the regulatory proteins involved in such cell cycle control, there are relatively few pronounced molecular changes which are known. Although some differences, such as altered glycosylation, have been observed on neoplastic cells, in general there are very few molecular markers that are specifically expressed on the surface of the neoplastic cell and therefore available for immunotherapeutic targeting. In contrast, many antigens which have been characterized in regard to tumor specific expression have been found to be only modestly selective between neoplastic and normal phenotypes. For these reasons, it is extremely laborious to find antigens which are specific to neoplastic cells.

It has now been observed by the inventors that one consequence of neoplastic transformation is a metabolic imbalance which results in altered sorting and trafficking of intracellular membrane proteins of the lysosomal and endocytic pathways. Lysosomal proteins are either soluble or membrane-associated. Both types of proteins are synthesized on the rough endoplasmic reticulum similar to other proteins of the secretory pathway. Following synthesis they are then transported, or sorted, to the lysosome. The same is true for other proteins of the endocytic pathway. The term "sorted" is used when discussing the accurate transport of these proteins to the lysosome since other alternative pathways exist. Such other pathways include, for example, transport to the plasma membrane or secretion into the extracellular space.

The sorting of either soluble or membrane lysosomal proteins occurs by very distinct mechanisms. For example, soluble lysosomal enzymes are sorted from the Golgi apparatus to the lysosomes through association of phosphorylated carbohydrate moieties with a specific receptor. These phosphorylated moieties are high mannose-type asparagine-linked oligosaccharide modifications of the protein core. Accordingly, the receptor for these oligosaccharide structures is the mannose 6-phosphate receptor (MPR). Recognition of mannose 6-phosphate by MPR occurs in the lumen of the Golgi apparatus. Bound by MPR, the soluble lysosomal enzymes are sorted to prelysosomal compartments where they are then released due to the acidic environment. Although the MPR directs soluble lysosomal enzymes to lysosomes, it is not itself a lysosomal membrane protein.

Once dissociated in the prelysosomal compartment, it recycles to the Golgi complex. Some MPR can also be found on the plasma membrane where it functions to deliver lysosomal enzymes from the extracellular environment back to the lysosomes through the endocytic pathway. The subcellular localization of MPR is in large part unchanged with neoplastic transformation.

Although it has been observed that several soluble lysosomal enzymes are secreted at elevated levels in neoplastic cells, by virtue of their very different sorting mechanism there have been no generalizations that sorting, much less sorting of membrane proteins of the lysosomal and endocytic compartments are a result of neoplastic transformation. In contrast to the MPR-dependent sorting of soluble lysosomal enzymes, lysosomal membrane proteins are sorted through a MPR-independent mechanism. Recognition of a specific cytoplasmic amino acid sequence directs these transmembrane proteins to the lysosome. Although the presence of minor levels of lysosomal membrane proteins has been observed on the plasma membrane, this observation has been attributed to either the assumption of a saturable receptor to the cytoplasmic recognition sequence or to more physiologically relevant events such as those requiring exocytosis (Fukuda, M., *J. Biol. Chem.* 266:21327–21330 (1991)).

The saturable receptor hypothesis has been put forth as an attempt to explain why in normal cells variable levels of plasma membrane expression can be observed with certain lysosomal membrane proteins. Some support for this hypothesis has now been provide by artificially overexpressing transfected cDNAs encoding lysosomal membrane proteins or by mutating the cytoplasmic recognition sequence (Harter and Mellman, J. *Cell. Biol.* 117:311–325 (1992)).

In the cases of more physiological relevance, it has been observed that lysosomal proteins can be detected on the surface following platelet activation and cytotoxic T cell exocytosis of granule contents during specific interaction with target cells. The normal occurrence of lysosomal membrane proteins on the plasma membrane therefore appears to be a consequence of membrane fusion. However, the presence of these proteins on the surface can also be to provide protection for the plasma membrane from the actions of the released lysosomal acid hydrolyses. Nevertheless, in either of the above cases, what is observed is a low and variable level of expression of lysosomal membrane proteins on the surface in normal cells. Because of this variability, there has been no direct correlation of the presence of lysosomal membrane proteins to particular cell lineages or to particular cell phenotypes.

As stated previously, it has now been observed that one consequence of neoplastic transformation is a metabolic imbalance which results in altered sorting and trafficking of membrane proteins of the lysosomal and endocytic pathways. This metabolic imbalance leads to the increased expression of these normally intracellular proteins on the plasma membrane surface of the neoplastic cell. These relocalized lysosomal membrane proteins are, however, not permanently localized to the plasma membrane. Instead, they still exhibit normal cyclization properties and can be internalized where they find their way back to endocytic vesicles.

This aberrant sorting phenotype has two characteristics that can be advantageously exploited in the neoplastic cell for the beneficial targeting of therapeutic agents. First, the lysosomal membrane proteins are specifically expressed on the plasma membrane of neoplastic cells at high and discriminatory levels compared to normal cells. This characteristic allows for the specific targeting of therapeutic agents through binding agents which specifically recognize the lysosomal membrane protein or other protein of the endocytic pathway. The second characteristic is that since these otherwise aberrantly located lysosomal or vesicular membrane proteins are essentially normal, they internalize the binding agent. This internalization not only allows the use of toxins which function intracellularly, but, will also significantly decrease the toxic effects to neighboring cells when using pleiotropic or ablative agents such as radioisotopes. It is these properties which lead to the terminology of these lysosomal and other endocytic membrane proteins as being neoplastic cell specific internalizing antigen.

The methods of the invention target cytotoxic or cytostatic agents to neoplastic cells through the use of binding agents which are specific to the neoplastic cell specific internalizing antigens. As defined above, such binding agents can be essentially any molecule, including peptide, polypeptide and protein or other macromolecules or binding compounds which exhibit specific binding activity toward the neoplastic cell specific internalizing antigen. In the specific case where the neoplastic cell specific internalizing antigen is a transmembrane protein, the binding agent will be reactive to the lumenal domain of the protein since this is the domain that will be exposed to the extracellular environment once the lysosomal or other endocytic vesicles have fused with the plasma membrane.

Cytotoxic or cytostatic agents are attached to the binding agents by a variety of methods known in the art. Attachment, coupling or conjugation can be accomplished by, for example, covalent bond formation; however, other means known in the art can be equally applied as well. Essentially any type of coupling methodology will work so long as conditions are used to maintain the functions of both of the binding agent and the cytotoxic or cytostatic agent. Such methods are well known in the art and are described in, for example, Harlow et al. (*Antibodies: A Laboratory Manual,* Cold Spring Harbor (1988)). For example, the covalent bond can be formed by way of carbodiimide, glutaraldehyde, heterobifunctional cross-linkers, and homobifunctional cross-linkers. The cross-linking of proteins can additionally be accomplished by using reactive groups within the individual protein such as carbohydrate, disulfide, carboxyl or amino groups. Coupling can be accomplished by oxidation or reduction of the native protein, or treatment with an enzyme, for example.

Similarly, numerous different cytotoxic and cytostatic agents are known by those skilled in the art. Selection of which cytotoxic or cytostatic agent to use will depend on the need and will be known, or can be determined by those skilled in the art. For example, cisplatin based regimens are utilized for ovarian, esophageal cancer, head and neck cancer, non-small cell lung cancer and testicular cancer.

In non-small cell lung cancer, cisplatin combined with vinca alkaloids and mitomycin CMVP resulted in a 77% major response rate. Platinum containing complexes represent the most important group of agents now in use for cancer treatment. They can be curative in combination therapy for testicular and ovarian cancers and play a central role in the treatment of lung, head and neck, and bladder cancers members of this group have desirable pharmacologic action including synergy in combination with antimetabolites and radiation therapy but differ significantly in their patterns of toxicity and pharmacokinetics. Thus, the cytotoxic or cytostatic agents can range from small organic molecules to large biologically active proteins and other macromolecules.

To reduce proliferation of a neoplastic cell, the cytotoxic or cytostatic agent and the binding agent are attached, or conjugated, to one another to produce a cytotoxic or cytostatic binding agent. The binding agent is chosen so as to be specifically reactive with one or more neoplastic cell specific internalizing antigens present on the surface of the neoplastic cell. These therapeutic binding agents are then placed in contact with the neoplastic cells and allowed to bind the neoplastic cell specific internalizing antigen. Once bound, the cytotoxic or cytostatic binding agent will be internalized through the endocytic pathway.

For cytotoxic agents which result in non-specific destruction of the cell, such as radioactive isotopes, once bound to the neoplastic cell specific internalizing antigen they will immediately exert their effect on inhibiting cell proliferation. Internalization of such cytotoxic agents, however, reduces the ablative effects on neighboring, normal cells. In contrast, when using cytotoxic or cytostatic agents which are effective only once they become internalized, such as toxins which ribosylate the protein synthesis machinery, targeting of neoplastic cell specific internalizing antigens ensures that such agents will enter the cytoplasm and become effective. These antigens will undergo a sufficient rate of internalization and therefore are not reliant upon secondary mechanisms such as the steady-state recycling of plasma membrane to deliver the cytotoxic or cytostatic agent to the cytoplasm.

The methods of the invention utilize aberrantly expressed vesicular membrane associated neoplastic cell specific internalizing antigens. Such antigens include, for example, those known lysosomal membrane proteins which are categorized in the lamp-2 or limp II families as well as those categorized in these families and other families which are subsequently identified as having substantially the same characteristics of neoplastic cell specific internalizing antigen as defined previously. Further, other membrane proteins of the endocytic pathway which exhibit, or are found to exhibit the characteristics described previously are also considered to be useful in the methods of the invention. Such other proteins include, for example, p110, vacuolar-$H^+$-ATPase, acetyl CoA:α-glucosaminide N-acetyltransferase, prosaposin, procathepsin L receptor and lysosomal acid phosphatase. Thus, the invention provides for a method of reducing the proliferation of a neoplastic cell by contacting the cell with a cytotoxic or cytostatic binding agent that is specifically reactive with any of the above neoplastic cell specific internalizing antigens.

The invention also provides a method for intracellular targeting of a cytotoxic or cytostatic agent to a neoplastic cell population. The method comprises administering to an individual containing a neoplastic cell population, or suspected of containing a neoplastic cell population, a cytotoxic or cytostatic binding agent specifically reactive with an aberrantly expressed vesicular membrane associated neoplastic cell specific internalizing antigen expressed by the neoplastic cell population, wherein said cytotoxic or cytostatic binding agent is bound by the neoplastic cell specific internalizing antigen and is internalized into the intracellular compartment.

The invention also provides for a method of reducing the growth of a tumor through the intracellular targeting of a cytotoxic or cytostatic agent. The method consists of administering to an individual containing, or suspected of containing a tumor, a cytotoxic or cytostatic binding agent specifically reactive with an aberrantly expressed vesicular membrane associated neoplastic cell specific internalizing antigen expressed by cells of the tumor wherein the cytotoxic or cytostatic binding agent is bound by the neoplastic cell specific internalizing antigen and is internalized into the intracellular compartment.

The methods described previously for reducing the proliferation of a neoplastic cell are applicable for in vitro diagnosis of neoplastic cells or the testing of various agents applicable to both the ex-vivo and in vivo targeting of therapeutic agents to neoplastic cell populations. Such methods are useful, for example, for testing the cytotoxic or cytostatic effects of specific agents in vitro, bone marrow purging ex vivo and for inhibiting the growth of single or small populations of metastatic cells at secondary tumor sites. Similarly, the methods describe previously are equally applicable for inhibiting proliferation and/or viability of larger neoplastic cell populations or solid tumors, for example. In these specific examples, the cytotoxic or cytostatic binding agent is administered in a therapeutically effective dose so as to circulate and bind the neoplastic cell specific internalizing antigen which is specific for the tumor cell of interest. Once bound, the cytotoxic or cytostatic agent will be internalized to specifically reduce the growth of the neoplastic cell population or tumor mass expressing the targeted internalizing antigen.

The cytotoxic or cytostatic agents are administered to an individual exhibiting or at risk of exhibiting cells having a neoplastic phenotype. Definite clinical diagnosis of neoplasia warrants the administration of one or more cytotoxic or cytostatic binding agents to the relevant neoplastic cell specific antigen. Prophylactic applications are warranted in cases where there is a genetic disposition to develop neoplasia or where there is a possibility that secondary metastasis or recurrence of the original growth can occur.

Cytotoxic or cytostatic binding agents can be administered in many possible formulations, including pharmaceutically acceptable media. In the case of a short peptide, the peptide can be conjugated to a carrier, for example, in order to increase its stability within the circulatory system. Antibodies are advantageous for use as a binding agent since they are naturally long-lived proteins of the circulatory system. Antibodies can be produced in a variety of mammals and then genetically engineered to resemble proteins of human origin and in this way avoid endogenous host defense mechanisms. Methods for "humanization" of antibodies are well known in the art and are described, for example, in Winter and Harris, Immunol. Today, 14:243–246 (1993);

Winter and Harris, Tips, 14:139–143 (1993) and Couto et al. Cancer Res., 55:1717–1722 (1995).

The cytotoxic or cytostatic binding agents are administered by conventional methods, in dosages which are sufficient to effect binding of the neoplastic cell specific internalizing antigen. Such dosages are known or can be easily determined by those skilled in the art. Administration can be accomplished by, for example, intravenous, interperiential or subcutaneous injection. Administration can be performed in a variety of different regimes which include single high dose administration or repeated small dose administration or a combination of both. The dosing will depend on the type of neoplasia, progression of the disease and overall health of the individual and will be known or can be determined by those skilled in the art.

The cytotoxic or cytostatic binding agent can be administered to an individual either singly or in a cocktail containing two or more cytotoxic or cytostatic binding agents, other therapeutic agents, compositions, or the like, including, for example, immunosuppressive agents, potentiators and side-effect relieving agents. Immunosuppressive agents include for example, prednisone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators include, for example, monensin, ammonium chloride and chloroquine. All of these agents are administered in generally accepted efficacious dose ranges such as those disclosed in the Physician Desk Reference, 41st Ed. (1987), Publisher Edward R. Barnhart, New Jersey.

The cytotoxic or cytostatic binding agents can be formulated into, for example, injectable or topical preparation for administration. Parenteral formulations are known and are suitable for use in the invention, preferably for i.m. or i.v. administration. Formulations containing therapeutically effective amounts of the cytotoxic or cytostatic binding agents can be sterile liquid solutions, liquid suspensions or lyophilized versions and can additionally contain stabilizers or excipients for example. Therapeutically effective doses of the cytotoxic or cytostatic binding agents can be, for example, in a range of from about less then 0.01 mg/kg to about greater than 10 mg/kg body weight of the treated individual administered over several days to two weeks by daily intravenous infusion.

The cytotoxic or cytostatic binding agents can be formulated into topical preparations for local therapy by including it. The cytotoxic or cytostatic binding agents can be formulated into topical preparations for local therapy by including it in a dermatological vehicle. The amount of agent to be administered will depend upon the vehicle selected, the clinical condition of the patient, the systemic toxicity and the stability of the anti-T cell immunotoxin in the formulation. Suitable vehicles include for example, gels or water-in-oil emulsions using mineral oils, petrolatum and the like.

Cytotoxic or cytostatic binding agents can also be administered by aerosol to achieve localized delivery to the lungs. This is accomplished by preparing an aqueous aerosol, liposomal preparation or solid particles containing or derivatives thereof. Ordinarily, an aqueous aerosol is made by formulating an aqueous solution or suspension of the cytotoxic or cytostatic binding agents together with conventional pharmaceutically acceptable carriers and stabilizers. The carriers and stabilizers will vary depending upon the requirements for the particular binding agent but include, for example, nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. The formulations also can include mucolytic agents as well as bronchodilating agents. The formulations will be sterile. Aerosols generally will be prepared from isotonic solutions. The particles optionally include normal lung surfactants.

It is understood that modifications which do not substantially affect the activity of the various embodiments of this invention are also included within the definition of the invention provided herein. Accordingly, the following examples are intended to illustrate but not limit the present invention.

EXAMPLE I

Altered Trafficking of Membrane-Associated Lysosomal Proteins

This example shows that membrane-associated lysosomal proteins are mistargeted to the plasma membrane in carcinoma cells.

Demonstration of the mistargeting of membrane-associated lysosomal proteins to the cell surface was shown using two different approaches. In the first approach, monoclonal antibodies specific for different membrane-associated lysosomal proteins (Table 1) are utilized in an ELISA format with either normal or carcinoma cells obtained from a variety of human tissues (Table 2). In order to measure only the antigen present on the cell surface, cells are plated in 96-well microtiter dishes one day prior to determining antibody reactivity. On the next day, cells are rinsed with phosphate-buffered saline (PBS), and incubated with dilutions of each antibody in 1% bovine serum albumin (BSA) in PBS for one hour. The cells are gently washed with PBS and incubated an additional one hour with biotinylated anti-mouse IgG (or other appropriate specificity). The cells are washed with PBS and then incubated with biotinylated horseradish peroxidase-avidin complexes (ABC staining kit, Pierce) for 15 minutes. Unbound complex is removed with several PBS washes. All antibody incubations and wash steps are performed at 4° C. After the final PBS wash the binding of antibody is detected by the addition of o-phenylenediamine hydrochloride. The reaction is terminated by the addition of 2.5 M $H_2SO_4$ and the formation of product is measured by adsorption at 492 nm. In order to measure non-specific binding of the secondary antibodies and avidin complexes one sample is incubated without primary antibody.

A second approach is utilized to measure specific cell surface expression of membrane-associated lysosomal proteins on non-adherent cells, such as peripheral blood lymphocytes. Briefly, a suspension containing $10^6$ cells/ml of culture media are incubated for one hour with 10 μg/ml of either primary antibody or an isotype-matched control antibody. Cells are pelleted, washed with 1% BSA in PBS, and incubated with fluoroscein isothiocyanate (FITC)-labeled anti-mouse IgG antibody for one hour. The cells are washed and analyzed for antibody binding by fluorescent activated cell sorting (FACS). All incubations and washes are performed at 4° C. Reactivity is expressed as the binding ratio of the test antibody (mean fluorescent intensity) versus the control antibody. Analysis of the results of the above assays will reveal significant and discriminatory binding on the carcinoma cell lines with little binding on the normal human cells.

EXAMPLE 2

Lysosomal Proteins Mistargeted to the Plasma Membrane are Internalized

This example demonstrates that membrane-associated lysosomal proteins expressed on the cell surface are rapidly internalized to an acidic vesicular compartment.

To demonstrate the dual localization of antigens at the plasma membrane and the lysosomes, double-label immunofluorescence is employed. Initially, the cell surface localization of antigens obtained by ELISA and FACS analysis is first confirmed by immunofluorescence on non-permeabilized cells. Briefly, monolayers of cells are seeded on coverslips one day prior to use. The next day, cells are rinsed with ice-cold PBS and fixed with 2% paraformaldehyde in PBS for 15 minutes at room temperature. The cells are rinsed twice with PBS and incubated one hour with primary antibody at 10 μg/ml in 1% BSA in PBS. As a positive control for plasma membrane localization, some cells are incubated with anti-transferrin receptor antibody. The cells are then washed with PBS, incubated with FITC-labeled anti-mouse IgG antibody for one hour and washed with PBS again. Little non-specific binding of FITC-labeled secondary antibody is observed in samples in which the primary antibody is omitted from the incubations. The coverslips are mounted in Fluoromount-G, to minimize florescent quenching, and examined with a Zeiss microscope equipped with epifluorescent optics and a Zeiss Plan 100× (NA 1.3) oil objective lens.

The intracellular localization of these same antigens is examined as described above with minor modifications. Specifically, 0.1% digitonin is included in all buffers used for antibody dilutions and cell washes. Digitonin selectively interacts with cholesterol, preserving the structure of most membranes while permeabilizing them sufficiently to allow the introduction of antibodies to intracellular structures. Permeabilized cells incubated with the test antibodies will display punctate staining distributed around the cell nuclei consistent with lysosomal localization. To further verify this, permeabilized cells are probed with antibodies against soluble lysosomal proteins (cathepsins B, D, and L) and examined for co-localization with the antibodies against the membrane-associated lysosomal proteins.

To determine internalization of such lysosomal membrane-associated proteins which have been redistributed to the plasma membrane, the above described procedure is used with yet some more minor modifications. Specifically, cells which have been seeded on coverslips one day prior are chilled on ice for 30–60 minutes to inhibit endocytosis. The cells are then washed with ice-cold PBS and 10 μg/ml antibody diluted in ice-cold cell culture media is added and incubated with the cells for one hour. The cells are washed with ice-cold PBS and incubated with FITC-labeled anti-mouse IgG antibody for 30 minutes. It is critical to maintain the cells at 4° C. for all preceding steps to insure that endocytosis is completely inhibited. Excess antibody is removed with additional PBS washes and the cells are then shifted to 37° C. by placing pre-warmed media on the dish. Incubations are stopped at various intervals by shifting the cells back to 4° C. and fixing the cells with 2% paraformaldehyde in PBS. Internalization to pre-lysosomal compartments is monitored with antibodies to the transferrin receptor while internalization to the lysosomal compartment is monitored with cathepsin D antibodies.

Analysis of the results of the above procedure will initially show diffuse surface binding of the antibodies, followed shortly thereafter by patching or congregation at multiple sites on the cell surface. With longer incubation times, the patches of antibodies will cap (localize to a single site on the cell surface) and begin to be internalized. Depending on the duration of incubation at 37° C., antibodies will co-localize either with the pre-lysosomal endocytic marker (transferrin receptor) or with the lysosomal marker, cathepsin D. Little or no staining is observed with (1) control primary antibodies, (2) if cells are incubated with secondary antibody only, or (3) if the cells are maintained at 4° C. for the duration of the experiment.

A further showing that these antibodies are being internalized can be obtained through the use of a functional assay which measures cell proliferation. Briefly, immunoconjugates of antibody and the toxin ricin A-chain, which must be internalized to be effective, are synthesized. Inhibition of proliferation in the presence of such cytotoxic binding proteins is measured using a [$^3$H]thymidine uptake assay.

In order to perform this assay, cells are seeded in a 96-well microtiter plate one day prior to the experiment. After removing the culture media, titrations of the antibody ricin A-chain immunoconjugates in culture media are added to the cells and incubated at 37° C. for 6 hours. Next, 1 μCi/well of [$^3$H]thymidine is added and the cells are incubated for an additional 6 hours at 37° C. The cells are frozen, thawed, harvested onto glass filters, and counted in a beta counter. Inhibition of the incorporation of [$^3$H]thymidine into cellular DNA in treated cells, as compared to untreated control cells, is consistent with the internalization of the antibodies observed by immunofluorescence.

To demonstrate the specificity of the cytotoxicity, carcinoma cells are treated with similar doses of a control antibody ricin A-chain immunoconjugate. Moreover, fibroblast cells which are shown by ELISA to express little of the targeted lysosomal membrane proteins on the plasma membrane are more resistant to the cytotoxic effects of the ricin A-chain immunoconjugates and display cytotoxicity profiles similar to those obtained with irrelevant immunoconjugates.

EXAMPLE 3

Treatment of Xenografted Human Carcinomas with Doxorubicin Immunoconjugates

This example demonstrates the ability of antibodies to neoplastic cell specific internalizating antigens to efficiently target solid tumors in vivo.

The antibodies of Table 1 are conjugated to doxorubicin, or another suitable cytoxic agent, via an acid-labile linker. For example, midocaproyl doxorubicin hydrazone derivatives have been shown to provide suitable plasma stability while allowing the release of the cytotoxic agent in the acidic intracellular environment of the endosomes/ lysosomes.

Human carcinoma lines which are demonstrated to be reactive with the primary antibody by ELISA, FACS, immunofluorescence, and the functional internalization assay, are grown as subcutaneous implants in athymic mice. In one set of control animals, implants of tumor lines not reactive with the primary antibody are established. All tumors are established for 14–28 days, at which time the animals are treated with multiple doses of (1) the doxorubicin immunoconjugates, (2) doxorubicin conjugated to a control antibody, or (3) doxorubicin alone. Doses are matched on the basis of mg doxorubicing/kg body weight. Following treatment, efficacy is measured as partial regression (decrease in tumor volume to less than 50% of original volume), complete regression (not observable for defined time), or cured (not observable for greater than 10 doubling times). One doubling time is defined as the time required for tumors in control (untreated) animals to double in size. Animals treated with optimal doses of control immunoconjugates or doxorubicin alone will display fewer partial regressions, complete regressions, or cures than mice which are treated with the doxorubicin immunoconjugates utilizing the internalizing antigens described herein. In addition, higher maximum tolerable doses of doxorubicin are achieved with the immunoconjugates of internalizing lysosomal antigens than is achievable with free doxorubicin.

TABLE 1

Membrane-associated Lysosomal Protein Targets

| Class | Target |
|---|---|
| lamp-2 | lamp-2 |
| limp II | limp II |
|  | CLA-1 |
| NA | p110 |
| NA | 64 kDa chloride channel |

TABLE 1-continued

Membrane-associated Lysosomal Protein Targets

| Class | Target |
|---|---|
| NA | vacuolar-H$^+$-ATPase |
| NA | lysosomal acid phosphatase |

TABLE 2

Cell Lines Analyzed In Vitro

| Type | Tissue | Name | ATCC No. |
|---|---|---|---|
| carcinoma | breast | MDA-MB-231 | HTB 26 |
| carcinoma | colon | COLO 205 | CCL 222 |
| carcinoma | colon | DLD-1 | CCL 221 |
| carcinoma | colon | HCT-15 | CCL 225 |
| carcinoma | colon | SW 1417 | CCL 238 |
| carcinoma | kidney | ACHN | CRL1611 |
| carcinoma | lung | A549 | CCL 185 |
| carcinoma | ovary | Caov-4 | HTB 76 |
| carcinoma | pancreas | PANC-1 | CRL1469 |
| carcinoma | thyroid | SW 579 | HTB 107 |
| normal | colon | CCD-18Co | CRL1459 |
| normal | lung | CCD-18Lu | CCL 205 |
| normal | peripheral blood | lymphocytes | NA |

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of reducing the proliferation of a neoplastic cell, comprising contacting the neoplastic cell with a cytotoxic or cytostatic binding agent specifically reactive with a neoplastic cell specific internalizing antigen, said antigen associated with vesicular membranes in non-neoplastic cells and expressed at elevated levels on the plasma membrane of neoplastic cells as compared to non-neoplastic cells, whereby said binding agent is bound by said antigen and internalized into said neoplastic cell.

2. The method of claim 1, wherein said neoplastic cell specific internalizing antigen is selected from the group consisting of lamp-2 and limp II families of lysosomal integral membrane proteins and excluding lamp-1 tumor associated antiqens.

3. The method of claim 1, wherein said neoplastic cell specific internalizing antigen is selected from the group consisting of p110, vacuolar-H$^+$-ATPase, acetyl CoA:α-glucosaminide N-acetyltransferase, prosaposin, procathepsin L receptor and lysosomal acid phosphatase.

4. The method of claim 1, wherein said cytotoxic or cytostatic binding agent is an antibody specific to the lumenal domain of the neoplastic cell specific internalizing antigen.

5. A method of intercellular targeting a cytotoxic or cytostatic agent to a neoplastic cell population, comprising administering to an individual a cytotoxic or cytostatic binding agent specifically reactive with a neoactive cell specific internalizing antigen, said antigen associated with vesicular membranes in non-neoplastic cells and expressed at elevated levels on the plasma membrane of neoplastic cells as compared to non-neoplastic cells, whereby said binding agent is bound by said antigen and internalized into said neoplastic cell population.

6. The method of claim 5, wherein said neoplastic cell specific internalizing antigen is selected from the group consisting of lamp-2 and limp II families of lysosomal integral membrane proteins and excluding lamp-1 tumor associated antigens.

7. The method of claim 5, wherein said neoplastic cell specific internalizing antigen is selected from the group consisting of p110, vacuolar-$H^+$-ATPase, acetyl CoA:α-glucosaminide N-acetyltransferase, prosaposin, procathepsin L receptor and lysosomal acid phosphatase.

8. The method of claim 5, wherein said cytotoxic or cytostatic binding agent is an antibody specific to the lumenal domain of the neoplastic cell specific internalizing antigen.

9. A method of reducing the growth of a tumor through the intracellular targeting of a cytotoxic agent, comprising administering to an individual a cytotoxic or cytostatic binding agent specifically reactive with a neoplastic cell specific internalizing antigen, said antigen associated with vesicular membranes in non-neoplastic cells and expressed at elevated levels on the plasma membrane of neoplastic cells as compared to non-neoplastic cells, whereby said binding agent is bound by said antigen and is internalized into a cell of said tumor.

10. The method of claim 9, wherein said neoplastic cell specific internalizing antigen is selected from the group consisting of lamp-2 and limp II families of lysosomal integral membrane proteins and excluding lamp-1 tumor associated antigens.

11. The method of claim 9, wherein said neoplastic cell specific internalizing antigen is selected from the group consisting of p110, vacuolar-$H^+$-ATPase, acetyl CoA:α-glucosaminide N-acetyltransferase, prosaposin, procathepsin L receptor and lysosomal acid phosphatase.

12. The method of claim 9, wherein said therapeutic binding agent further comprises a cytotoxic or cytostatic binding agent.

13. The method of claim 9, wherein said cytotoxic or cytostatic binding agent is an antibody specific to the lumenal domain of the neoplastic cell specific internalizing antigen.

* * * * *